(12) United States Patent
Thomas et al.

(10) Patent No.: US 11,327,065 B1
(45) Date of Patent: May 10, 2022

(54) PREPARATION OF ANGIOTENSIN RECEPTOR BLOCKERS OR PHARMACEUTICALLY ACCEPTABLE SALTS THEREOF

(71) Applicant: Jubilant Generics Limited, Noida (IN)

(72) Inventors: Saji Thomas, Noida (IN); Rajendra Shekhawat, Noida (IN); M. Umamaheshwar Prasad, Noida (IN); Bidyut Biswas, Noida (IN); Rohit Chakravarthy, Noida (IN); Chetan Balubhai Patel, Mysore (IN); Anilkumar Haribhat Lingabhat, Mysore (IN); Mohan Chikmagalur Sadashivappa, Mysore (IN); Indranil Nandi, Yardley, PA (US)

(73) Assignee: Jubilant Generics Limited

( * ) Notice: Subject to any disclaimer, the term of this patent is extended or adjusted under 35 U.S.C. 154(b) by 0 days.

(21) Appl. No.: 17/459,374

(22) Filed: Aug. 27, 2021

(51) Int. Cl.
| | | |
|---|---|---|
| G01N 33/15 | (2006.01) | |
| G01N 30/72 | (2006.01) | |
| C07D 403/02 | (2006.01) | |
| C07D 403/10 | (2006.01) | |
| G01N 30/02 | (2006.01) | |

(52) U.S. Cl.
CPC ........... *G01N 33/15* (2013.01); *C07D 403/10* (2013.01); *G01N 30/7233* (2013.01); *G01N 2030/027* (2013.01)

(58) Field of Classification Search
CPC ... G01N 33/15; G01N 30/7233; C07D 403/10
USPC ................................................. 436/106, 173
See application file for complete search history.

(56) References Cited

U.S. PATENT DOCUMENTS

| | | | | |
|---|---|---|---|---|
| 5,153,197 | A * | 10/1992 | Carini | C07D 231/12 514/254.05 |
| 5,310,928 | A * | 5/1994 | Lo | C07F 5/05 548/250 |
| 5,608,075 | A * | 3/1997 | Campbell, Jr. | A61P 9/12 548/252 |
| 2003/0078435 | A1* | 4/2003 | Fischer | A61P 9/12 548/253 |
| 2004/0034077 | A1* | 2/2004 | Dolitzky | C07D 403/10 514/381 |
| 2006/0287537 | A1* | 12/2006 | Radi | C07D 257/04 548/253 |
| 2010/0190996 | A1* | 7/2010 | Veera Reddy | C07D 403/10 548/252 |
| 2010/0222597 | A1* | 9/2010 | Veera Reddy | C07D 403/10 548/252 |

OTHER PUBLICATIONS

Reddy, V. V. et al, Asian Journal of Chemistry 2007, 19, 3789-3796.*
Prasaja, B. et al., Journal of Pharmaceutical and Biomedical Analysis 2009, 49, 862-867.*
Thomas, S. et al, Journal of Pharmaceutical and Biomedical Analysis 2012, 57, 39-51.*
Madasu, S. B. et al, Organic Process Research & Development 2012, 16, 2025-2030.*
Tengli, A. R. et al, American Journal of Analytical Chemistry 2015, 6, 228-238.*
Gricar, M. et al, Journal of Pharmaceutical and Biomedical Analysis 2016, 125, 27-32.*

(Continued)

*Primary Examiner* — Arlen Soderquist
(74) *Attorney, Agent, or Firm* — William D. Hare, Esq.; McNeely, Hare & War, LLP

(57) ABSTRACT

The present invention relates to a process for the preparation of angiotensin receptor blockers or its pharmaceutically acceptable salts thereof containing less than 10 ppm of the azido impurities. More particularly, the present invention relates to process for the preparation of Losartan, Losartan potassium of Formula I or its other pharmaceutically acceptable salts thereof containing less than 10 ppm of each of the azido impurities, wherein the azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole. More particularly, the present invention relates to a simple, economical and industrially efficient process for the preparation of Losartan potassium of Formula I.

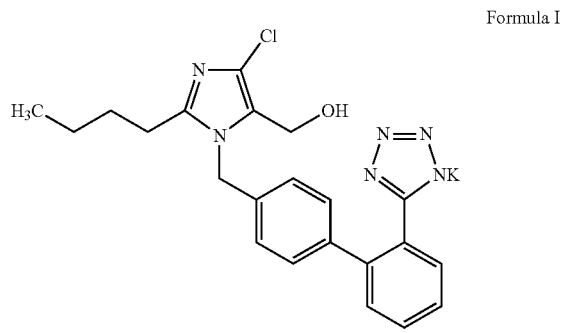

Formula I

20 Claims, No Drawings

(56) References Cited

OTHER PUBLICATIONS

Smerikarova, M. et al, Current Analytical Chemistry 2020, 16, 208-222.*
Shelke, M. et al, Critical Reviews in Analytical Chemistry 2020, 50, 226-253.*
Jires, J. et al, Journal of Pharmaceutical and Biomedical Analysis 2021, 205, paper 114300, 6 pages.*

* cited by examiner

PREPARATION OF ANGIOTENSIN RECEPTOR BLOCKERS OR PHARMACEUTICALLY ACCEPTABLE SALTS THEREOF

FIELD OF THE INVENTION

The present invention relates to a process for the preparation of angiotensin receptor blockers or its pharmaceutically acceptable salts thereof. More particularly, the present invention relates to a simple, economical and industrially efficient process for the preparation of Losartan potassium of Formula I.

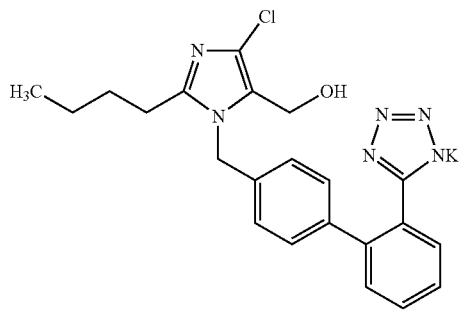

Formula I

BACKGROUND OF THE INVENTION

The chemical name for Losartan is (2-butyl-4-chloro-1-{[2'-(2H-tetrazol-5-yl)biphenyl-4-yl]methyl}-1H-imidazol-5-yl)methanol. The CAS Registry Number of Losartan is [114798-26-4], which has the following structure.

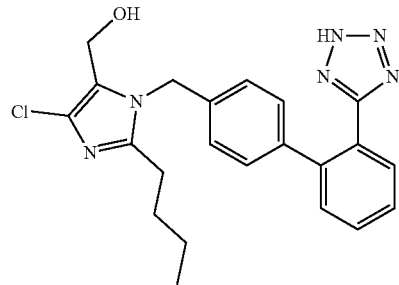 [SMILES: CCCCc1nc(Cl)c(CO)n1Cc1ccc(-c2ccccc2-c2nn[nH]n2)cc1]

Losartan and its potassium salt are angiotensin-II receptor (Type AT1) antagonists. In adults Losartan is currently indicated for the treatment of hypertension. The incidence of hypertension is very high with every third person in the world is suffering from this condition. This provides a huge market potential for antihypertensive drugs. Due to its high market value over the world, cost effective synthesis of Losartan is highly desirable.

U.S. Pat. No. 5,138,069 discloses and claims Losartan, its derivatives and pharmaceutically acceptable salts, including the potassium salt, as well as a method of treatment using pharmaceutically acceptable salts of Losartan. This patent also discloses a process for the preparation of Losartan and its derivatives, which comprises de-protecting trityl-Losartan with hydrochloric acid to form free base of Losartan, and then adding aqueous potassium hydroxide-isopropanol solution to convert the free base to its potassium salt.

The known processes suffer from problems of purity of Losartan or its pharmaceutically acceptable salts thereof regarding presence of undesirable carcinogenic azido impurities. The processes disclosed in the prior art fail to provide the control of carcinogenic/genotoxic azido impurities.

Azido impurities such as 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole, 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole, which are highly mutagenic/genotoxic/carcinogenic and are point of concern. The processes for the preparation of Losartan disclosed in the prior arts fail to provide the control of said carcinogenic/genotoxic azido impurities.

Consequently, there is a need for an improved process for the preparation of Losartan or its pharmaceutically acceptable salts thereof, which not only overcomes the problems in the prior art processes as mentioned above, but also is simple, economically viable, industrially feasible and environment friendly for the preparation of Losartan or its pharmaceutically acceptable salts thereof having a good control over carcinogenic/genotoxic azido impurities and its carcinogenic precursor impurities.

In view of the same, there is a need for simple, industrially feasible, cost effective and environmentally-friendly process for the preparation of Losartan or its pharmaceutically acceptable salts thereof free from carcinogenic/genotoxic azido impurities and its carcinogenic precursor impurities.

The problem has been solved by providing an improved process, wherein Losartan or its pharmaceutically acceptable salts thereof is heated in the presence of solvent with aqueous alkali to isolate pure Losartan or its pharmaceutically acceptable salts thereof, which is free from carcinogenic/genotoxic azido impurities and its carcinogenic precursor impurities.

OBJECT OF THE INVENTION

It is a principal object of the present invention to improve upon limitations of the prior arts by providing an efficient process for the preparation of Losartan and/or pharmaceutically acceptable salts thereof.

It is another object of the present invention to provide a simple, commercially viable, economical and environment friendly process for preparing Losartan and/or pharmaceutically acceptable salts thereof.

The present invention relates to a process for the preparation of angiotensin receptor blockers namely Losartan, Valsartan, Candesartan, Olmesartan or Irbesartan or its pharmaceutically acceptable salts thereof containing less than 10 ppm of the azido impurities.

It is still another object of the present invention to provide an improved process for the preparation of Losartan or its pharmaceutically acceptable salts thereof containing less than 10 ppm of each of the carcinogenic azido impurity, wherein azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole.

It is still another object of the present invention to provide Losartan or its pharmaceutically acceptable salts thereof containing less than 10 ppm of each of the undesirable carcinogenic azido impurity, wherein azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole.

It is still another object of the present invention to provide an improved process for the preparation of Losartan or its pharmaceutically acceptable salts thereof containing less than 10 ppm of each of the carcinogenic azido impurity by heating Losartan or its pharmaceutically acceptable salts thereof in solvent with aqueous alkali to isolate Losartan or its pharmaceutically acceptable salts thereof free from carcinogenic azido impurities.

It is still another object of the present invention to provide an improved process for the preparation of Losartan or Losartan potassium containing less than 10 ppm of each of the carcinogenic azido impurity by heating Losartan or Losartan potassium in solvent with aqueous alkali to isolate Losartan or Losartan potassium free from carcinogenic azido impurities.

SUMMARY OF THE INVENTION

The present invention relates to a process for the preparation of angiotensin receptor blockers namely Losartan, Valsartan, Candesartan, Olmesartan or Irbesartan or its pharmaceutically acceptable salts thereof containing less than 10 ppm of the azido impurities.

According to one aspect of the present invention there is provided an efficient and cost effective process for the preparation of Losartan or its pharmaceutically acceptable salts thereof containing less than 10 ppm of each of the carcinogenic azido impurity, wherein azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole.

It has been found that Losartan or its pharmaceutically acceptable salts thereof containing less than 10 ppm of each of the carcinogenic azido impurity is efficiently prepared by heating Losartan or its pharmaceutically acceptable salts thereof in solvent with aqueous alkali.

Heating Losartan or its pharmaceutically acceptable salts thereof, preferably potassium salt, in solvent with aqueous alkali helps in achieving Losartan or its pharmaceutically acceptable salts thereof containing less than 10 ppm of each of the carcinogenic azido impurity.

DESCRIPTION OF THE INVENTION

The present invention relates to a process for the preparation of angiotensin receptor blockers namely Losartan, Valsartan, Candesartan, Olmesartan or Irbesartan or its pharmaceutically acceptable salts thereof containing less than 10 ppm of the each of the azido impurities.

Azido impurities of Losartan or Losartan potassium are highly mutagenic/genotoxic/carcinogenic and are point of concern during the synthesis of angiotensin receptor blockers. These azido impurities are:

5-(4'-(azidomethyl)-[1,1'-biphenyl]-2-yl)-1H-tetrazole of Formula II

4'-(azidomethyl)-[1,1'-biphenyl]-2-carbonitrile of Formula III,

4'-((5-(azidomethyl)-2-butyl-4-chloro-1H-imidazol-1-yl)methyl)-[1,1'-biphenyl]-2-carbonitrile of Formula IV, 5-(4'-((5-(azidomethyl)-2-butyl-4-chloro-1H-imidazol-1-yl)methyl)-[1,1'-biphenyl]-2-yl)-1H-tetrazole of Formula V, 5-(azidomethyl)-2-butyl-4-chloro-1H-imidazole of Formula VI, 4'-((4-(azidomethyl)-2-butyl-5-chloro-1H-imidazol-1-yl)methyl)-[1,1'-biphenyl]-2-carbonitrile of Formula VII, 5-(4'-((4-(azidomethyl)-2-butyl-5-chloro-1H-imidazol-1-yl)methyl)-[1,1'-biphenyl]-2-yl)-1H-tetrazole of Formula VIII and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole of Formula IX.

Formula II

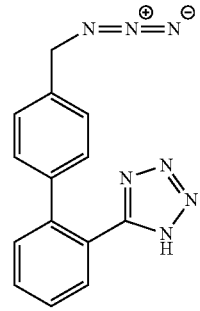

-continued

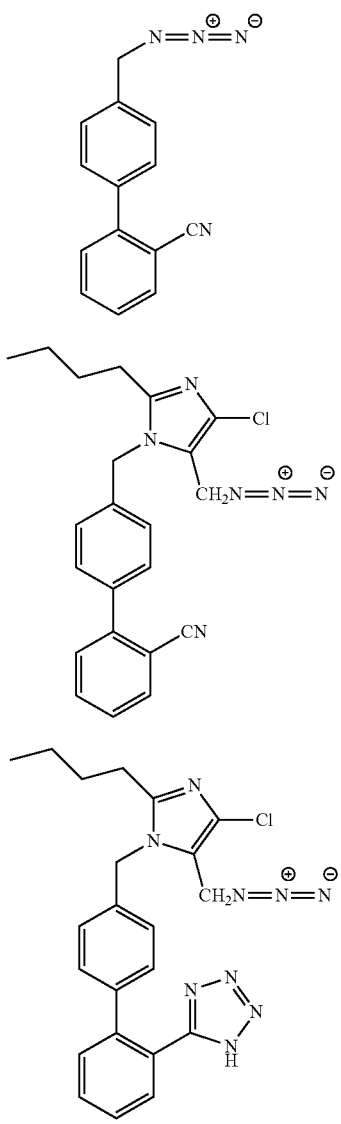

Formula III

Formula IV

Formula V

Formula VI

Formula VII

-continued

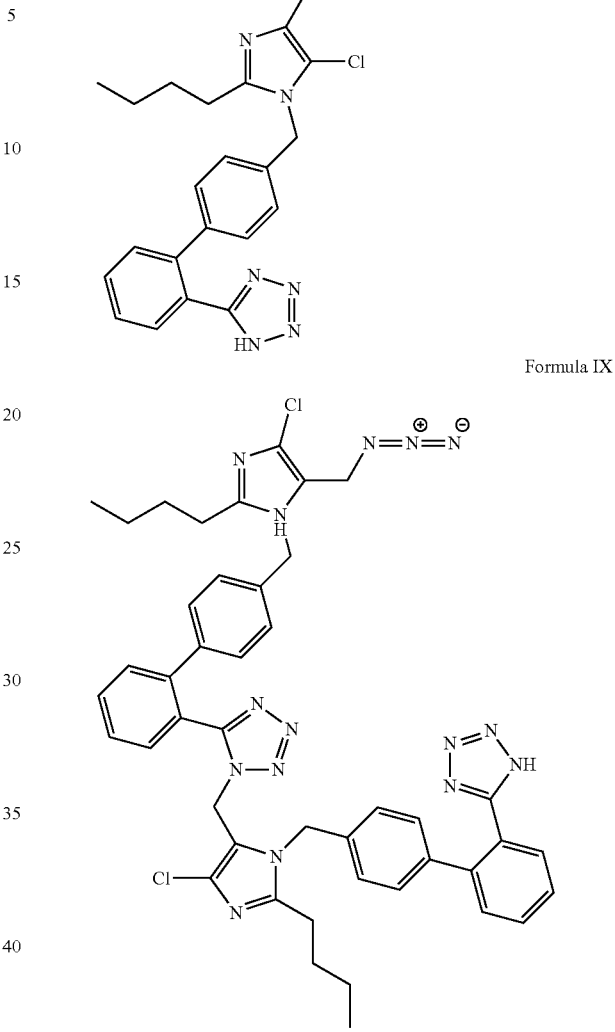

Formula VIII

Formula IX

As per ICH M7, based on the maximum daily dose of 150 mg/day for Losartan Potassium, the acceptable intake for each individual mutagenic impurity is less than 10 ppm.

In an embodiment, the present invention relates to a process for the preparation of Losartan or its pharmaceutically acceptable salts thereof containing less than 10 ppm of each of the azido impurity, wherein azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azido methyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((14(2'-(1H-tetrazol-5-yl)-[1,1'-biphenyl]-4-yl)methyl)-2-butyl-4-chloro-1H-imidazol-5-yl) methyl)-5-(4'-((5-(azidomethyl)-2-butyl-4-chloro-1H-imidazol-1-yl)methyl)-[1,1'-biphenyl]-2-yl)-1H-tetrazole comprising the steps of:

(i) providing a solution of Losartan or its pharmaceutically acceptable salts thereof in solvent with aqueous alkali;
(ii) heating the reaction mixture; and
(iii) isolating Losartan or its pharmaceutically acceptable salts thereof.

In step (i), solvent is selected from the group comprising of water, organic solvent and mixtures thereof. The organic solvent is selected from the group comprising of hydrocarbon solvent, polar aprotic solvent, polar protic solvent, non-polar solvent and the like. The organic solvent is further selected from the group comprising of pentane, hexane, 1,4-dioxane, diethyl ether, tetrahydrofuran (THF), ethyl acetate, toluene, xylene, acetone, dimethylformamide (DMF), acetonitrile (ACN), methanol, ethanol, propanol, n-butanol and the like.

In step (i), the alkali is selected from the group comprising of sodium hydroxide, potassium hydroxide, lithium hydroxide, calcium hydroxide and magnesium hydroxide. Alkali in step (i) is preferably sodium hydroxide or potassium hydroxide.

In step (i), the concentration of aqueous sodium or potassium hydroxide solution is selected from 0.5% to 35%. Concentration of aqueous sodium or potassium hydroxide solution is preferably 2.5% to 5.0%.

In step (i), mole equivalents of alkali with respect to Losartan is from 0.1 to 5 mole equivalents.

Alternatively, potassium iodide, sodium iodide and the like can also be used along with aqueous sodium hydroxide solution for depletion of azido impurities.

Alternatively reducing agents such as sodium borohydride, lithium borohydride and the like can also be used along with an aqueous base solution for depletion of the azido impurities.

In step (ii), heating is carried out at a temperature from 40° C. to 110° C. Heating in step (ii) is carried out preferably at a temperature from 90° C. to 100° C.

In step (ii), heating is carried out for 8 hours to 24 hours, preferably 10 hours to 15 hours.

In step (iii), isolation is performed by conventional means already known in the prior art which includes is but not limited to filtration, distillation, crystallization, acid-base treatment and the like, preferably filtration.

As per instant invention, the Limit of Detection (LOD) for these azido impurities is 1 ppm.

In an embodiment, the present invention relates to a process for the preparation of Losartan or its pharmaceutically acceptable salts thereof containing less than 10 ppm of each of the azido impurity, wherein azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl) methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl) methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azido methyl)-2-butyl-4-chloro-1H-imidazol-1-yl)methyl)-[1,1'-biphenyl]-2-yl)-1H-tetrazole comprising the steps of:
(i) providing a solution of Losartan or its pharmaceutically acceptable salts thereof in solvent with aqueous alkali;
(ii) heating the reaction mixture;
(iii) isolating Losartan or its pharmaceutically acceptable salts thereof; and
(iv) optionally repetition of steps (i) to (iii), to obtain Losartan or its pharmaceutically acceptable salts thereof having azido impurity less than 10 ppm.

In an embodiment, the present invention relates to a process for the preparation of Losartan or its pharmaceutically acceptable salts thereof containing less than 10 ppm of each of the azido impurities, wherein the azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azido methyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1, 1'-biphenyl]-2-carbonitrile, 5-(4'-((4-(azidomethyl)-2-butyl-5-chloro-1H-imidazol-1-yl) methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azido methyl)-2-butyl-4-chloro-1H-imidazol-1-yl)methyl)-[1,1'-biphenyl]-2-yl)-1H-tetrazole comprising the steps of:
(i) providing a solution of Losartan or its pharmaceutically acceptable salts thereof in solvent with aqueous alkali;
(ii) heating the reaction mixture;
(iii) adding organic solvent and adjusting pH 3 to 5 by means of adding acid to the reaction mixture;
(iv) filtering the reaction mixture; and
(v) isolating Losartan or its pharmaceutically acceptable salts thereof.

In step (ii), heating is carried out at temperature from 40° C. to 110° C., preferably at a temperature from 90° C. to 100° C.

In step (ii), heating is carried out for 8 hours to 24 hours, preferably 10 hours to 15 hours.

In an another embodiment, the present invention relates to a process for the preparation of Losartan potassium containing less than 10 ppm of each of the azido impurities, wherein the azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azido methyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl) methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole comprising the steps of:
(i) providing a solution of Losartan potassium in water with potassium hydroxide;
(ii) heating the reaction mixture to 90° C. to 100° C.; and
(iii) isolating Losartan potassium containing less than 10 ppm of each of the azido impurities.

In an another embodiment, the present invention relates to a process for the preparation of Losartan or Losartan potassium containing less than 10 ppm of 5-(4'-((5-(azidomethyl)-2-butyl-4-chloro-1H-imidazol-1-yl)methyl)-[1,1'-biphenyl]-2-yl)-1H-tetrazole of Formula V, comprising the steps of:

(i) providing a solution of Losartan or Losartan potassium in solvent with aqueous alkali;

(ii) heating the solution at a temperature from 40° C. to 110° C. for 8 hrs to 24 hrs; and (iii) isolating Losartan or Losartan potassium.

ICH M7 recommends that these mutagenic carcinogens be controlled at or below the acceptable cancer risk level. Due to their known potent carcinogenic effects, and because it is feasible to limit these impurities by taking reasonable steps to control or eliminate their presence, the goal is to have no quantifiable carcinogenic impurities or well within the declared limits which is safe for human consumption.

It is utmost important to control or deplete these undesirable carcinogenic azido impurities such as 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole below 10 ppm in Losartan or its pharmaceutically acceptable salts thereof.

In an another embodiment, the present invention relates to a process for the preparation of Losartan potassium containing less than 10 ppm of each of the azido impurity.

It has been found that purification techniques like dissolving Losartan or Losartan potassium in water and washing with organic solvent such as methyl iso-butyl ketone, dichloromethane, heptane, toluene or ethyl acetate did not efficiently remove the carcinogenic azido impurities.

TABLE 1

Depletion of mutagenic azido impurity by dissolving Losartan potassium in water and washing with organic solvent

| Process | Azido impurity of Formula V (ppm) | |
|---|---|---|
| | Initial | After washing |
| Dissolving Losartan potassium in 3 V of purified water and washing with methyl isobutyl ketone | 315 | 190 |
| Dissolving Losartan potassium in 3 V of purified water and washing with dichloromethane | 315 | 169 |
| Dissolving Losartan potassium in 3 V of purified water and washing with n-heptane | 315 | 197 |
| Dissolving Losartan potassium in 3 V of purified water and washing toluene | 315 | 190 |
| Dissolving Losartan potassium in 3 V of purified water and washing with ethyl acetate | 315 | 188 |

The present applicant has found that desired limit of azido impurities was not achieved when aqueous solution of Losartan potassium was extracted with organic solvents.

TABLE 2

Depletion of mutagenic azido impurity by crystallization of Losartan potassium

| Solvent | Initial Azido impurity of Formula II content (ppm) | Final Azido impurity of Formula II content (ppm) |
|---|---|---|
| IPA/n-Heptane | 428 | 157.5 |
| IPA | 204 | 137.25 |
| Ethyl acetate | 452.19 | 278.3 |

TABLE 3

Depletion of mutagenic azido impurity by crystallization of Losartan

| Batch Size (g) | Solvent | Output (g) | Azido impurity of Formula V content in input (ppm) | Azido impurity of Formula V content after crystallization (ppm) |
|---|---|---|---|---|
| 4.0 | Ethyl acetate | 3.5 | 802.32 | 657 |
| 4.0 | Methyl isobutyl ketone | 3.6 | 802.32 | 657 |
| 4.0 | Isopropyl alcohol | 2.0 | 802.32 | 657 |
| 30.0 | Ethyl acetate/water/HCl | 26 | 802.32 | 638 |
| 5.0 | Isopropyl alcohol/water | 3.0 | 802.32 | 638 |
| 5.0 | Ethyl acetate | 2.5 | 802.32 | 638 |

The present applicant has found that desired limit of azido impurities was not achieved by crystallization of Losartan or Losartan potassium using different solvents and/or mixture thereof.

TABLE 4

Content of various azido impurities in Losartan while heating with Potassium carbonate To Losartan, 5 volumes of 20% of aqueous Potassium carbonate was added and it was heated at 95° C.-100° C. for 14 hr.

| Azido impurity - input (before treatment) | Azido impurity after treatment |
|---|---|
| 1845.8 ppm | 1838.5 ppm |

The present applicant has found that there was no depletion of azido impurity in Losartan when heated in aqueous potassium carbonate solution.

TABLE 5

Content of various azido impurities in Losartan potassium while heating with Potassium carbonate To Losartan potassium, 5 volumes of 20% of aqueous Potassium carbonate was added and it was heated at 95° C.-100° C. for 14 hr.

| Azido impurity - input (before treatment) | Azido impurity after treatment |
|---|---|
| 601.7 ppm | 617.3 ppm |

The present applicant has found that there was no depletion of azido impurity in Losartan potassium when heated in aqueous potassium carbonate solution.

TABLE 6

Content of various azido impurities in Losartan and
Losartan potassium by employing the process of the instant invention
Azido impurity of Formula V content (in ppm)

| Input Batch size | Azido impurity during reaction monitoring by HPLC | After heating in aqueous potassium hydroxide solution for 10-12 h at 95-100° C., followed by isolation of Losartan |
|---|---|---|
| 50 g | 3324 ppm | Less than 1 ppm |
| 50 g | 3019 ppm | Less than 1 ppm |

The problem has been solved by providing an improved process in which Losartan or its pharmaceutically acceptable salts thereof in solvent with aqueous alkali is heated and Losartan or its pharmaceutically acceptable salts thereof containing less than 10 ppm of each of the azido impurity is isolated.

The analytical method used for the determination of azido impurities in Losartan or pharmaceutically acceptable salts thereof is either LCMS/LCMS-MS method or HPLC method. The analytical method used for the determination of azido impurities during reaction monitoring is HPLC method. The analytical method used for the determination of azido impurities in isolated Losartan or its pharmaceutically acceptable salts thereof is LCMS or LCMS-MS method.

Specifically, analytical method for the determination of azido impurities in Losartan or its pharmaceutically acceptable salts thereof is LCMS or LCMS-MS method, wherein azido impurity is selected from the group comprising of 5-(4'-(azidomethyl)-[1,1'-biphenyl]-2-yl)-1H-tetrazole, 4'-(azidomethyl)-[1,1'-biphenyl]-2-carbonitrile, 4'-((5-(azidomethyl)-2-butyl-4-chloro-1H-imidazol-1-yl)methyl)-[1,1'-biphenyl]-2-carbonitrile, 5-(4'-((5-(azidomethyl)-2-butyl-4-chloro-1H-imidazol-1-yl)methyl)-[1,1'-biphenyl]-2-yl)-1H-tetrazole, 5-(azidomethyl)-2-butyl-4-chloro-1H-imidazole, 4'-((4-(azidomethyl)-2-butyl-5-chloro-1H-imidazol-1-yl)methyl)-[1,1'-biphenyl]-2-carbonitrile, 5-(4'-((4-(azidomethyl)-2-butyl-5-chloro-1H-imidazol-1-yl)methyl)-[1,1'-biphenyl]-2-yl)-1H-tetrazole and 1-((1-((2'-(1H-Tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole.

LCMS-MS method: Azido impurities in Losartan or Losartan potassium was determined by LCMS-MS method using ESI mode with mobile phase.

Mobile phase (water/methanol): 720 mL/1280 mL methanol and 0.1% formic acid Using Column: Xbridge C8 150×4.6, 5µ, Flow rate 0.8 mL/min HPLC method: Azido impurities in Losartan or Losartan potassium was determined by HPLC method with mobile phase 10 mM phosphate buffer and 0.1% OPA, column Xterra RP18, 250×4.5, 5µ column temperature 40° C., isocratic method with buffer and methanol.

The process for the preparation of Losartan or its pharmaceutically acceptable salts thereof as described in the present invention is demonstrated in the examples illustrated below. Certain specific aspects and embodiments of the present application are explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

EXAMPLES

Example-1: Preparation of (14(2'-(1H-Tetrazol-5-yl) (1,1'-biphenyl)4-yl)methyl)-2-butyl-4-chloro-1H-imidazol-5-yl)methanol Tetrazole ring formation of 4'-{[2-Butyl-4-chloro-5-(hydroxymethyl)-1H-imidazole-1-yl] methyl} biphenyl-2-carbonitrile (100 g) was performed using sodium azide (2.98 mole equivalent), triethylamine hydrochloride (3.30 mole equivalent), triethylamine (1.08 mole equivalent) and methyl isobutyl ketone (1.5V) as solvent. The reaction mass was heated at 95° C.-110° C. and maintained for 30 hr-35 hr. After reaction, the organic layer was extracted with aqueous Potassium hydroxide solution. To the aqueous layer containing Losartan, 20% of Potassium hydroxide was added and this solution was heated to 95° C.-100° C. and stirred it for 12 hr-14 hr. After charcoalization of the aqueous layer, pH was adjusted to 3.8-4.2 with addition of dilute HCl in presence of ethyl acetate and stirred for 6 hr-7 hr at 0° C.-5° C. Next, the product was filtered, isolated and dried. The Losartan was further purified by heating in 3.9% KOH solution (5 V) at 95° C.-100° C. for 12 hr-14 hr followed by isolation by adjusting the pH to 3.8-4.2 with the addition of dilute HCl in the presence of ethyl acetate and stirred for 6 hr-7 hr at 0° C.-5° C. The product then was filtered, isolated and dried.

Azido impurity <1 ppm obtained from approximately 5,000-10,000 ppm formed during tetrazole reaction Example-2: Preparation of (1-((2'-(1H-Tetrazol-5-yl)(1,1'-biphenyl)4-yl)methyl)-2-butyl-4-chloro-1H-imidazol-5-yl)methanol Tetrazole ring formation of 4'-{[2-Butyl-4-chloro-5-(hydroxymethyl)-1H-imidazole-1-yl] methyl} biphenyl-2-carbonitrile (100 g) was performed using sodium azide (2.98 mole equivalent), triethylamine hydrochloride (3.30 mole equivalent), tetrabutyl ammonium bromide and methyl isobutyl ketone (5V) as solvent and with the reaction mass heated at 95° C.-110° C. and maintained for 30 hr-35 hr. After completion of the reaction, the product was extracted into aqueous layer using 10% aqueous sodium hydroxide solution and this aqueous solution was heated to 12 hr-24 hr at 95° C.-100° C. till the azido impurities wear below 10 ppm. The Losartan is isolated after the pH is adjusted to 3.8-4.2 with addition of dilute HCl in the presence of ethyl acetate and stirred for 6 hr-7 hr at 0-5° C. The product then is filtered and isolated. The product is dried initially at 25° C.-30° C. for 2 hr under vacuum and then at 60° C.-65° C. for 8 hr under vacuum.

Molar Yield: 90%; HPLC Purity >99.0%
Azido impurity: 8 ppm obtained from 5,000-10,000 ppm formed during tetrazole reaction Example-3: Preparation of Potassium 5-[4'-[[2-butyl-4-chloro-5-(hydroxymethyl)-1H-imidazol-1-yl]methyl]biphenyl-2-yl]tetrazol-1-ide (Losartan Potassium Salt Formation)

Charged IPA (8V) and 50% solution of KOH at 25° C.-30° C. Stirred the resulting mixture for 30 min to get a clear solution at 25° C.-30° C. Charged Losartan (100 g) at 25° C.-30° C. Stirred the reaction mass for 1 hr to get clear solution at 25° C.-30° C. Check pH (pH 9.5-10.0). Charged activated carbon (2.7%) at 25° C.-30° C. Stirred the reaction mass for 30 min at 25° C.-30° C. Filtered the resulting mixture through hyflo bed washed with IPA (2V). Distilled out the solvent to approximately 70%, atmospherically below 85° C. Cooled the reaction mass to 60° C.-65° C. under nitrogen. Charged n-Heptane (1V) at 60° C.-65° C. under nitrogen. Gradually cooled the reaction mass to 25° C.-30° C. in 2 hr-3 hr under nitrogen. Stirred the reaction mass at 25° C.-30° C. for 6 hr-7 hr under nitrogen. Gradually cooled the reaction mass in 2 hr-3 hr to 0-5° C. under nitrogen. Stirred the reaction mass at 0° C.-5° C. for 2 hr under nitrogen. Then the reaction mass was filtered and washed with chilled IPA (1V) under nitrogen. Suck dried and unloaded the wet product under nitrogen. Dried the product initially at 25° C.-30° C. for 2 hr and then at 60° C.-65° C. for 8 hr under vacuum.

Molar Yield: 90%; HPLC Purity >99.5%
Azido impurity <1 ppm.

Example-4

Charged 3.9% KOH Solution (19.5 g KOH Dissolved in DM water (500 mL). Charged Losartan potassium (100 g). Heated to 95° C.-100° C. and stirred for 12 hr-20 hr. Cooled reaction mixture to 10° C.-15° C. Charged ethyl acetate (300 mL) at 10° C.-15° C. Slowly adjusted the pH to 3.8-4.2 with dilute HCl. Raised temperature of reaction mass to 25° C.-30° C. Resulting mixture was stirred for 6 hr-7 hr at 25° C.-30° C. Cooled the reaction mass to 0° C.-5° C. and stirred for 2 hr at 0-5° C. Filtered it and washed with DM water (3×120 mL) and then with ethyl acetate (120 mL) at 25° C.-30° C. Suck dried the filtered product and unloaded wet product. Dried the product initially at 25° C.-30° C. under vacuum for 2 hr and then at 60° C.-65° C. under vacuum for 8 hr.

Molar Yield: 90%; HPLC Purity >99.5%
Azido Impurity <1 ppm;

Example-5

Charged 3.9% KOH Solution (19.5 g KOH Dissolved in DM Water (500 mL) and Losartan potassium (100 g). Heated to 95° C.-100° C. and stirred for 12 hr-20 hr. Cooled the reaction mixture to 10° C.-15° C. Charged ethyl acetate (300 mL) at 10° C.-15° C. Slowly adjusted the pH to 3.8-4.2 with dilute HCl. Raised temperature of reaction mass to 25° C.-30° C. Stirred resulting mixture for 6 hr-7 hr at 25° C.-30° C. Cooled reaction mass to 0° C.-5° C. and stirred for 2 hr at 0° C.-5° C. Filtered the material and washed with DM water (3×120 mL) and then ethyl acetate (120 mL) at 25° C.-30° C. Suck dried the filtered material and unloaded wet material. Dried the product initially at 25° C.-30° C. under vacuum for 2 hr and then at 60° C.-65° C. under vacuum for 8 hr till LOD is NMT 0.5%. Azido Impurity <1 ppm obtained from 200-500 ppm Losartan potassium.

Example-6

Charged IPA (8V) and 50% solution of KOH at 25° C.-30° C. Stirred the resulting mixture for 30 min to get clear solution at 25° C.-30° C. Charged Losartan potassium (100 g) at 25° C.-30° C. Stirred the reaction mass for 1 hr to get clear solution at 25° C.-30° C. Check pH (pH 9.5-10.0). Charged activated carbon (2.7%) at 25-30° C. Stirred the reaction mass for 30 min at 25-30° C. Filtered the resulting mixture through hyflo and hyflo bed washed with IPA (2V). The solvent was distilled out to approximately 70% atmospherically below 85° C. Cooled the reaction mass to 60° C.-65° C. under nitrogen. Charged n-Heptane(1V) at 60° C.-65° C. under nitrogen. Gradually cooled the reaction mass to 25° C.-30° C. in 2-3 hr under nitrogen. Stirred the reaction mass at 25° C.-30° C. for 6 hr-7 hr under nitrogen. Gradually cooled the reaction mass in 2 hr-3 hr to 0° C.-5° C. under nitrogen. Stirred the reaction mass at 0° C.-5° C. for 2 hr under nitrogen. Filtered the reaction mass and washed with IPA (1V) under nitrogen. Sucked dried and unloaded the wet material under nitrogen. Dried the product initially at 25° C.-30° C. for 2 hr and then at 60° C.-65° C. for 8 hr under vacuum.

Molar Yield: 85%; HPLC Purity >99.5%
Azido impurity <1 ppm

Example-7

Charged DM Water (500 mL) and Losartan Potassium (100 g) at 25° C.-30° C. A 20% aq. KOH solution (1.6 g KOH dissolved in DM water 8 mL) was added at 25° C.-30° C. Heated the reaction mixture to 95° C.-100° C. for 10 hr-12 hr. Distilled out DM water under vacuum below 80° C. till stir-able mass. Cooled the reaction mixture to 40° C. and added IPA (900 mL) and stirred for 15 min-30 min. Filtered the resulting mixture through hyflo bed, followed by filtration and washed with IPA (100 mL) at 40° C.-50° C. Charged clear filtrate into reactor at 25° C.-30° C. Distilled out IPA (~700 mL) atmospherically below 85° C. (maintained the residual volume-250 mL in the reactor). Cooled the reaction mass to 60° C.-65° C. under nitrogen. Charged n-heptane (50 mL) at 60° C.-65° C. under nitrogen. Gradually cooled the reaction mixture at 25° C.-30° C. in 2 hr-3 hr under nitrogen. Stirred the reaction mixture at 25° C.-30° C. for 6 hr-7 hr under nitrogen. Gradually cooled the reaction mixture in 2 hr-3 hr to 0° C.-5° C. under nitrogen. Stirred the reaction mixture at 0° C.-5° C. for 2 hr under nitrogen. Filtered the reaction mixture and washed with pre-filtered chilled (0° C.-5° C.) IPA (100 mL) under nitrogen. Sucked dried and unloaded the wet material under nitrogen. Dried the material initially at 25° C.-30° C. under vacuum for 2 hr and then at 60° C.-65° C. under vacuum for 8 hr.

Molar Yield: 90%; HPLC Purity >99.5%
Azido impurity <1 ppm obtained from 200-500 ppm Losartan Potassium.

The inventors have shown unexpected results in forming pure losartan and losartan potassium that have significantly reduced levels of azido impurities. The inventors have shown that numerous purification methods do not sufficiently reduce levels of the various azido impurities disclosed herein, including by (1) dissolving losartan potassium in water and washing with an organic solvent does not sufficiently reduce the azido impurities; (2) crystallization of losartan potassium from IPA/n-Heptane, IPA or ethyl acetate, methyl isobutyl ketone, ethyl acetate/water/HCl mixture, isopropyl alcohol/water mixture; and (3) heating of losartan or losartan potassium in aqueous potassium carbonate. To demonstrate the results of the purification methods according to the invention, the inventors have developed HPLC, LCMS, and LCMS-MS analytical methods specific for detecting and quantifying these impurities. In particular, the inventors have developed and used an HPLC analytical method for determining azido impurities during reaction monitoring and a LCMS or LCMS-MS analytical method for determining azido impurities in the isolated losartan or losartan salt.

Abbreviations Used Herein THF—tetrahydrofuran
DMF—dimethylformamide
ACN—acetonitrile
LOD—Limit of Detection
V—volume
IPA—isopropyl alcohol
DM water—demineralized water
KOH—potassium hydroxide
HCl—hydrochloric acid
NMT—not more than

What is claimed:

1. A process for the preparation of Losartan or its pharmaceutically acceptable salts thereof containing less than 10 ppm of any individual azido impurity, wherein the azido impurity is selected from the group consisting of:
    5-(4'-(azidomethyl)-[1,1'-biphenyl]-2-yl)-1H-tetrazole,
    4'-(azidomethyl)-[1,1'-biphenyl]-2-carbonitrile,
    4'-((5-(azidomethyl)-2-butyl-4-chloro-1H-imidazol-1-yl)methyl)-[1,1'-biphenyl]-2-carbonitrile,
    5-(4'-((5-(azidomethyl)-2-butyl-4-chloro-1H-imidazol-1-yl)methyl)-[1,1'-biphenyl]-2-yl)-1H-tetrazole,
    5-(azidomethyl)-2-butyl-4-chloro-1H-imidazole,
    4'-((4-(azidomethyl)-2-butyl-5-chloro-1H-imidazol-1-yl)methyl)-[1,1'-biphenyl]-2-carbonitrile,
    5-(4'-((4-(azidomethyl)-2-butyl-5-chloro-1H-imidazol-1-yl)methyl)-[1,1'-biphenyl]-2-yl)-1H-tetrazole, and
    1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-[1,1'-biphenyl]-2-yl)-1H-tetrazole
    comprising the steps of:
    (i) providing a solution of Losartan or its pharmaceutically acceptable salts thereof in a solvent with an alkali;
    (ii) heating the reaction mixture at a temperature of from 90° C. to 100° C.; and
    (iii) isolating Losartan or its pharmaceutically acceptable salts thereof.

2. The process according to claim 1, wherein the solvent in step (i) is selected from the group consisting of water, an organic solvent and mixtures thereof.

3. The process according to claim 1, wherein the alkali in step (i) is selected from the group consisting of sodium hydroxide, potassium hydroxide, lithium hydroxide, calcium hydroxide and magnesium hydroxide.

4. The process according to claim 1, wherein the alkali in step (i) is potassium hydroxide.

5. The process according to claim 1, wherein the heating in step (ii) is carried out for 8 hrs to 24 hrs.

6. The process according to claim 1, wherein the heating in step (ii) is carried out for 12 hrs to 15 hrs.

7. The process according to claim 1, wherein the process further comprises:
    repeating steps (i) to (iii), to obtain Losartan or its pharmaceutically acceptable salts thereof having any individual Azido impurity being less than 10 ppm.

8. The process according to claim 1, further comprising analyzing the Losartan or its pharmaceutically acceptable salts thereof for the azido impurities by LCMS-MS method.

9. A process for the preparation of Losartan or its pharmaceutically acceptable salts thereof containing less than 10 ppm of any individual azido impurity, wherein the azido impurity is selected from the group consisting of:
    5-(4'-(azidomethyl)-[1,1'-biphenyl]-2-yl)-1H-tetrazole,
    4'-(azidomethyl)-[1,1'-biphenyl]-2-carbonitrile,
    4'-((5-(azidomethyl)-2-butyl-4-chloro-1H-imidazol-1-yl)methyl)-[1,1'-biphenyl]-2-carbonitrile,
    5-(4'-((5-(azidomethyl)-2-butyl-4-chloro-1H-imidazol-1-yl)methyl)-[1,1'-biphenyl]-2-yl)-1H-tetrazole,
    5-(azidomethyl)-2-butyl-4-chloro-1H-imidazole,
    4'-((4-(azidomethyl)-2-butyl-5-chloro-1H-imidazol-1-yl)methyl)-[1,1'-biphenyl]-2-carbonitrile,
    5-(4'-((4-(azidomethyl)-2-butyl-5-chloro-1H-imidazol-1-yl)methyl)-[1,1'-biphenyl]-2-yl)-1H-tetrazole, and
    1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-1-[1,1'-biphenyl]-2-yl)-1H-tetrazole, the process comprising the steps of:
    (i) providing a solution of Losartan potassium in water with potassium hydroxide;
    (ii) heating the reaction mixture to 90° C. to 100° C.; and
    (iii) isolating Losartan potassium containing less than 10 ppm of each of the azido impurities.

10. The process according to claim 9, further comprising analyzing the Losartan or its pharmaceutically acceptable salts thereof for the azido impurities by LCMS-MS method.

11. A process for the preparation of Losartan or its pharmaceutically acceptable salts thereof containing less than 10 ppm of any individual azido impurity, wherein the azido impurity is selected from the group consisting of:
    5-(4'-(azidomethyl)-[1,1'-biphenyl]-2-yl)-1H-tetrazole,
    4'-(azidomethyl)-[1,1'-biphenyl]-2-carbonitrile,
    4'-((5-(azidomethyl)-2-butyl-4-chloro-1H-imidazol-1-yl)methyl)-[1,1'-biphenyl]-2-carbonitrile,
    5-(4'-((5-(azidomethyl)-2-butyl-4-chloro-1H-imidazol-1-yl)methyl)-[1,1'-biphenyl]-2-yl)-1H-tetrazole,
    5-(azidomethyl)-2-butyl-4-chloro-1H-imidazole,
    4'-((4-(azidomethyl)-2-butyl-5-chloro-1H-imidazol-1-yl)methyl)-[1,1'-biphenyl]-2-carbonitrile,
    5-(4'-((4-(azidomethyl)-2-butyl-5-chloro-1H-imidazol-1-yl)methyl)-[1,1'-biphenyl]-2-yl)-1H-tetrazole, and
    1-((1-((2'-(1H-tetrazol-5-yl)-[1,1'-biphenyl]-4-yl)methyl)-2-butyl-4-chloro-1H-imidazol-5-yl)methyl)-5-(4'-((5-(azidomethyl)-2-butyl-4-chloro-1H-imidazol-1-yl)methyl)-1-[1,1'-biphenyl]-2-yl)-1H-tetrazole, the process comprising the steps of:
    (i) providing a solution of Losartan or its pharmaceutically acceptable salts thereof in a solvent with an alkali;
    (ii) heating the reaction mixture of step (i);
    (iii) adding an organic solvent and adjusting the pH to a pH of 3 to 5 by adding an acid to the reaction mixture;
    (iv) filtering the reaction mixture of step (iii); and
    (v) isolating Losartan or its pharmaceutically acceptable salts thereof.

12. The process according to claim 11, wherein the heating in step (ii) is carried out at a temperature of from 40° C. to 110° C.

13. The process according to claim 11, wherein the heating in step (ii) is carried out at a temperature of from 90° C. to 100° C.

14. The process according to claim 11, wherein the heating in step (ii) is carried out for 8 hrs to 24 hrs.

15. The process according to claim 11, wherein the heating in step (ii) is carried out for 12 hrs to 15 hrs.

16. The process according to claim 11, wherein the process comprises:

(i) providing a solution of Losartan potassium in water with potassium hydroxide;
(ii) heating the reaction mixture of step (i) to 90° C. to 100° C.;
(iii) adding an organic solvent and adjusting the pH to a pH of 3 to 5 by means of adding hydrochloric acid to the reaction mixture;
(iv) filtering the reaction mixture of step (iii); and
(v) isolating Losartan potassium containing less than 10 ppm of each of the azido impurity.

17. The process according to claim 11, wherein the solvent in step (i) is selected from the group consisting of water, an organic solvent and mixtures thereof.

18. The process according to claim 11, wherein the alkali in step (i) is selected from the group consisting of sodium hydroxide, potassium hydroxide, lithium hydroxide, calcium hydroxide and magnesium hydroxide.

19. The process according to claim 11, wherein the alkali in step (i) is potassium hydroxide.

20. The process according to claim 11, further comprising analyzing the Losartan or its pharmaceutically acceptable salts thereof for the azido impurities by LCMS-MS method.

\* \* \* \* \*